United States Patent [19]

Bacus

[11] Patent Number: 4,887,892
[45] Date of Patent: Dec. 19, 1989

[54] METHOD AND METHOD AND APPARATUS FOR CONTROL OF LIGHT INTENSITY FOR IMAGE ANALYSIS

[75] Inventor: James W. Bacus, Hinsdale, Ill.

[73] Assignee: Cell Analysis Systems, Inc., Lombard, Ill.

[21] Appl. No.: 35,822

[22] Filed: Apr. 8, 1987

Related U.S. Application Data

[63] Continuation-in-part of Ser. No. 927,285, Nov. 4, 1986, which is a continuation-in-part of Ser. No. 794,937, Nov. 4, 1985, Pat. No. 4,741,043.

[51] Int. Cl.[4] .................. G02B 21/08; G06K 9/28; G01N 33/48; H04N 7/18
[52] U.S. Cl. ......................... 350/523; 382/6; 128/633; 356/39; 358/107; 364/413.01
[58] Field of Search ............ 250/205; 382/6; 350/523, 526, 528, 508, 502; 128/633; 356/39; 358/107

[56] References Cited

U.S. PATENT DOCUMENTS

| | | | |
|---|---|---|---|
| 3,421,808 | 1/1969 | Gottlieb | 350/523 |
| 4,113,344 | 9/1978 | Shoemaker | 350/523 |
| 4,363,532 | 12/1982 | Weber | 350/523 |
| 4,479,700 | 10/1984 | Abe | 350/523 |
| 4,505,555 | 3/1985 | Piller | 350/523 |
| 4,529,264 | 7/1985 | Schmidt et al. | 350/523 |
| 4,737,022 | 4/1988 | Faltermeier et al. | 350/518 |

FOREIGN PATENT DOCUMENTS 172617  9/1984  Japan ................... 350/523

Primary Examiner—Jon W. Henry
Attorney, Agent, or Firm—Fitch, Even, Tabin & Flannery

[57] ABSTRACT

An image apparatus for measuring true mass characteristics of the specimen in real time is provided with means for controlling the amount and intensity of background light so that the amount of light is held substantially constant and at a level providing reduced background and scattered light so that evaluations at different times on the same or on different image analysis apparatus of the same manufacture result in substantially identical measurements of mass. The light control for the conventional light microscope used with the image analysis apparatus includes four variables which are the light intensity of the light bulb, the size of the field iris, the size of the condenser iris, and the movement the condenser lenses in a vertical or "Z" direction for focus. Preferably, a fixed aperture means in the form of a cup attachment is secured to the condenser iris optics to provide a fixed size iris for the condenser. The controls for the variable condenser iris are opened wide so that the less size aperature in the fixed condenser iris is that which is controlling of the light passing through the condenser optics. The preferred attachment device is a cup-shaped member of one piece metal which is attached by a threaded fastener in a non-invasive manner to the bottom of the condenser iris and optics. A monitor displays the intensity of the background light as a numerical value and the intensity of the light bulb is adjusted to provide a substantially constant background light transmitted to a CCD sensor or camera.

8 Claims, 5 Drawing Sheets

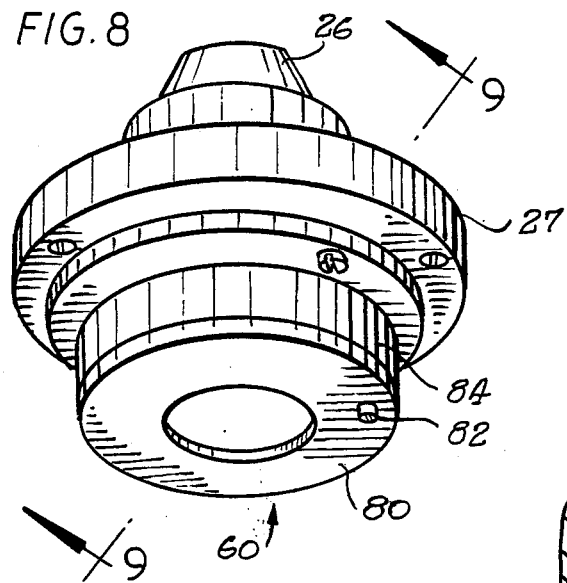
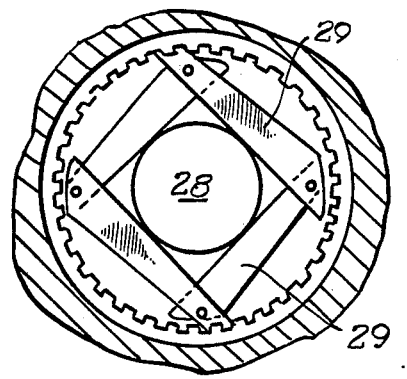
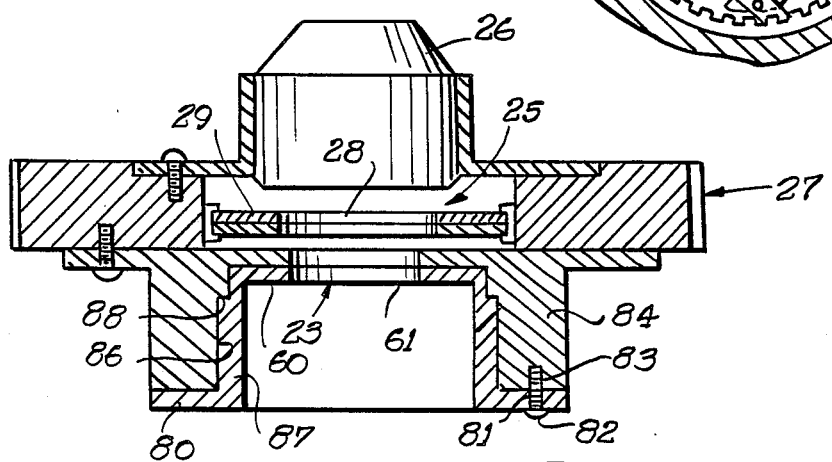
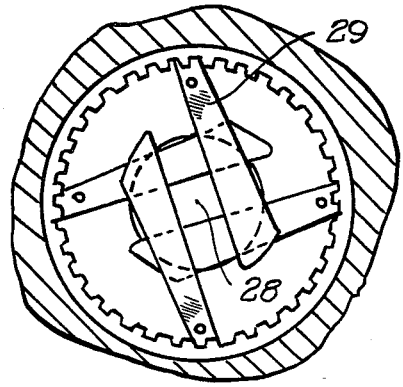

METHOD AND METHOD AND APPARATUS FOR CONTROL OF LIGHT INTENSITY FOR IMAGE ANALYSIS

This application is a continuation-in-part of copending patent application Ser. No. 927,285, filed Nov. 4, 1986 which in turn is a continuation-in-part of Ser. No. 794,937, filed Nov. 4, 1985, now U.S. Pat. No. 4,741,043.

This invention relates to a method of and apparatus for measuring cells with image analysis apparatus and more particularly to an improved light control method and apparatus for use in such image analysis apparatus.

The present invention is of particular use in a cell measuring apparatus using image analysis as disclosed in co-pending patent application Ser. No. 927,285, filed Nov. 4, 1986, which is hereby incorporated by reference as if fully reproduced herein. The present invention is not however limited to this specific apparatus disclosed in the aforesaid application because it has utility with other image analysis devices. The aforementioned patent application discloses in considerable detail an apparatus which measures the true optical density in mass units of a material in a cell such as DNA or hemoglobin in real time using a light microscope and a CCD camera which is receiving the image of the cell or cell nucleus for measuring DNA content in the cell nucleus or measuring the amount of hemoglobin present in red blood cells. The apparatus is also capable of detecting and measuring other materials associated with cells besides hemoglobin and DNA. The image analysis apparatus is to be used by pathologists or others who may not be highly trained in the use of such equipment so as to know how to control the light and the image reaching the CCD camera to produce the desired accurate, true mass unit measurements of DNA, hemoglobin, or other materials.

The present invention addresses the problem of how to mass produce cell measuring apparatus using image analysis employing a conventional, low cost, light microscope to illuminate the cells and to provide an enlarged image to the face of a CCD camera and to eliminate error in the mass measurements due to a high quantity of glare or background light being associated with the image or due to a non-uniform amount of light being used from one time to the next time or from one apparatus to another apparatus. The problem involves how to provide a uniform glare or background light at a minimal level so that the scattered light hitting the image area on the CCD camera is at a constant and a minimum or tolerable level. If the scattered light reduces the optical density significantly, then the true mass of the material in the cell may differ substantially from the mass which will be measured from the reduced density image.

Stated differently, the function of the light and optics in the image analysis apparatus is to map accurately the cell or nucleus image on the CCD camera and this is achieved by limiting the amount of light and the amount of scattered light that hits the CCD face. More specifically, due to the characteristics of the optics and the tubes involved, some scattered and background light will reach the pixels on the CCD camera face at which the pixels display an image resulting from the optical absorption of the mass of the material on the slide. The photons of scattered light which hit the pixels showing the cell are thus weakened and produce an optical density measurement less than is accurate. As will be explained, the present invention is initially calibrated to correct for a minimal amount of glare and it is desired that the apparatus be used at this calibrated or correct glare setting.

With the present invention, the optical density measured for a cell image is equal to the sum of the light measurements, that is the light absorption from all the pixels from a cell or specimen mounted on a transparent glass slide in the microscope. The amount of transmitted light through the cell mass or object may be defined as $T = I_t/I_o$ where $I_o$ is the light about the cell which has been produced by the light source and controlled by the field diaphragm, the condenser diaphragm, and condenser optics before hitting the microscope slide on which the cell is mounted in the aforesaid apparatus. As the thickness of the cell object increases, the transmitted light T falls off exponentially. To avoid the complicated calculations for thickness based on exponential calculations, the present invention, as more fully disclosed in the co-pending application, uses the log transform in which optical density (O.D.) equals $-\log[T]$. The log transforms are arranged in look-up tables in the digital computer and numbered 1 to 256 so that the output of the optical density from the CCD camera for a given pixel receives a digital number of between 1 to 256 and this is applied to a look-up table which provides an output log transformation and thereby an actual true optical density value to the digital computer. The look-up tables incorporate therein a glare correction to provide a calibrated optical density value which allows a true optical density reading for the specimen when the glare is at the calibrated setting. From the foregoing, it will be seen that the log transformation assumes that the background light $I_o$ is consistent because it is used as a constant denominator in the expression $T = I_t/I_o$. Unless the background light is carefully controlled to a substantially constant value, the same image on a slide could have different mass measurements from time to time on the same apparatus or two different apparatus having different background light. On the other hand, if the same slide is used in two different image apparatus of this type, each having the background light control of this invention, both apparatus should produce the same accurate and true mass units of hemoglobin or DNA.

Another factor involved in the accuracy of the actual mass units of DNA or hemoglobin being measured is that of light being passed through narrow band pass filters at wave lengths other than the peak wave, e.g. absorbed light for hemoglobin at a wave length 410. By a band pass width of 10 nanometers. The narrow band way of example, the light filters described herein have pass filter for DNA measurement has a 630 nanometer peak and a 10 nanometer narrow band pass. The width of the band pass filters are measured herein as being 10 nanometers wide at about 50 percent of the transmission peak when measured against the wave length in nanometers. Because these filters are not perfect in screening out all but 410 or 630 nanometer light, light at other wavelengths hits the CCD camera and there is response to this light wavelength because the CCD camera responds to light wave lengths in the range of 400 to 800 nanometers. Thus, it is desirable to reduce the amount of light being supplied because not all of the light has been filtered out by the filters. Stated differently, the more light that is let in by the bypass band filters, the more the light not at the selected peak wavelength is present to reduce the accuracy of the true mass units being measured.

In laboratory conditions where experts are employed to control the amount of light, they have a number of choices, including the changing of the lights to control its intensity or the use of different objective condenser lenses so as to use more accurate light sources and lenses. However, when it is desired to use a commercial and conventional light microscope in order to reduce the cost of the system, it is desired not to have a large number of different types of objective lenses or to have changes in light sources or other variables with which the user may not be familiar and may be unable to manipulate properly. With conventional light microscopes, there are four sources of light variation which are (1) the field diaphragm which changes the size of the cone of light in the typical light microscope; (2) a condenser optic or optics assembly which is movable in the Z or vertical direction to change the focus; (3) a condenser iris or diaphragm which is controlled in size by an adjustable knob, and (4) a light intensity control for changing the intensity of light from the light source. The condenser iris opening is generally reduced by about one-third from the maximum variable opening for the usual sizes of condenser lenses provided with the light microscope. However, the operator has nothing but manual vision as a guide in determining the size of the iris opening; and this is the most difficult variable to control of the four variables. The area of the opening of the condenser iris varies with the square of the radius of the opening so that minor differences in estimating the size of the iris opening diameter can result in significantly varying amounts of light passing through the condenser iris. Thus, the varying amounts of glare could, if not properly adjusted, close to the glare correction already in the look-up tables, result in error in the optical density readings for the specimen cells.

In accordance with an object of the present invention, there has been provided a new and improved, simplified control for the light used in image analysis apparatus for making true measurements of a cell constituent such as hemoglobin, DNA, or other materials.

Another object of the invention is to provide a low cost attachment to the apparatus disclosed in the aforesaid application which allows the control of the condenser iris and the amount of background light being transmitted.

A general object of the invention is to provide a new and improved light control method and apparatus in an image analysis cell measuring apparatus.

These and other objects and advantages of the invention will become apparent from the following detailed description, taken in conjunction with the accompanying drawings in which:

FIGS. 8, 9, 10 and 11 depict a condenser lens optics with a fixed iris attachment.

Figure 1:
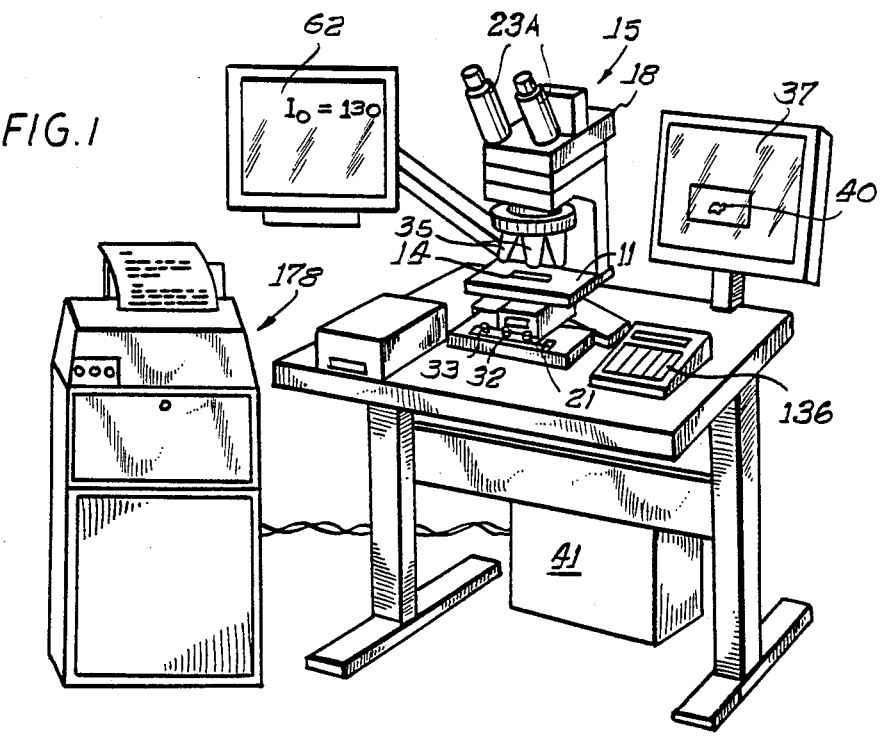
FIG. 1 is a view of the preferred apparatus having a light microscope and being operated in accordance with the novel features of the invention.

As shown in the drawings for purposes of illustration, the invention is embodied in a method and apparatus which is fully disclosed in Patent Application 927,285, filed Nov. 4, 1986, entitled "Analysis Method and Apparatus Method for Biological Specimens," the application and is incorporated by reference, and may be referred for further detailed description of the apparatus shown and described hereinafter.

As shown in the drawings for purposes of the illustration, the invention is embodied in an image display apparatus, such as shown in FIG. 1, which includes a conventional light microscope 15 of a generally commercially available type such as sold by the Reichert Company. As best seen in the FIGS. 1, 2 and 2A the microscope includes a stage or platform 11 on which is mounted the glass slide or support 14 which is preferably of a transparent glass material and is a common, commercially available specimen slide used for medical analysis. The slide 14 will typically contain a specimen 20 in the form of a cell which is being analyzed for a specific mass of materials such as DNA for a ploidy analysis for cancer or the amount of hemoglobin in a red blood the cell.

Figure 2:
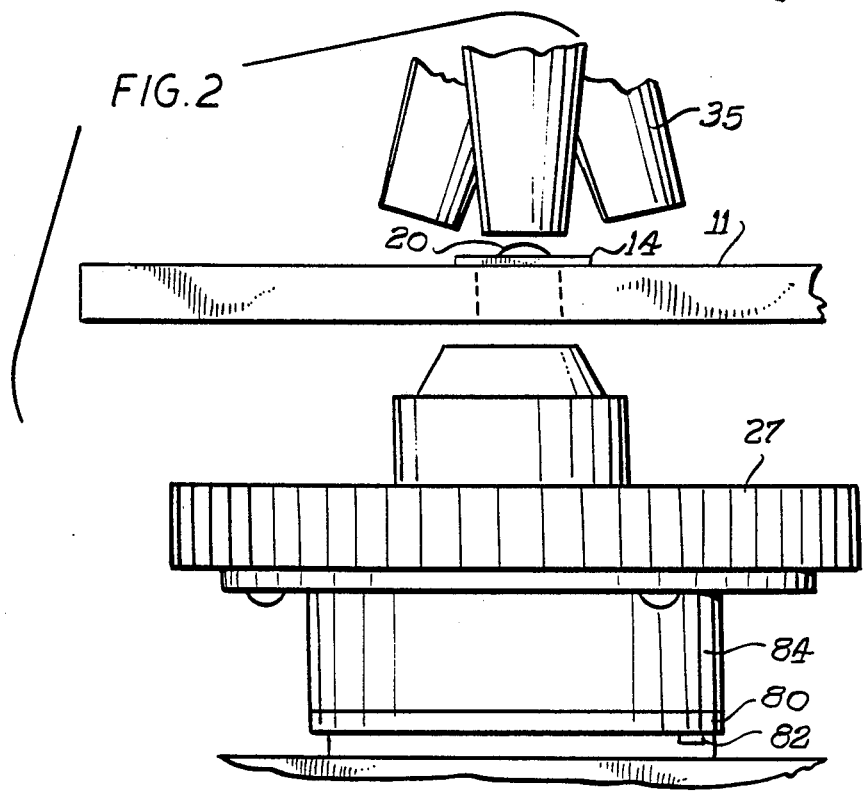
FIG. 2 is an enlarged view of the condenser optics and the slide on a stage of the light microscope shown in FIG. 1.
Figure 2A:
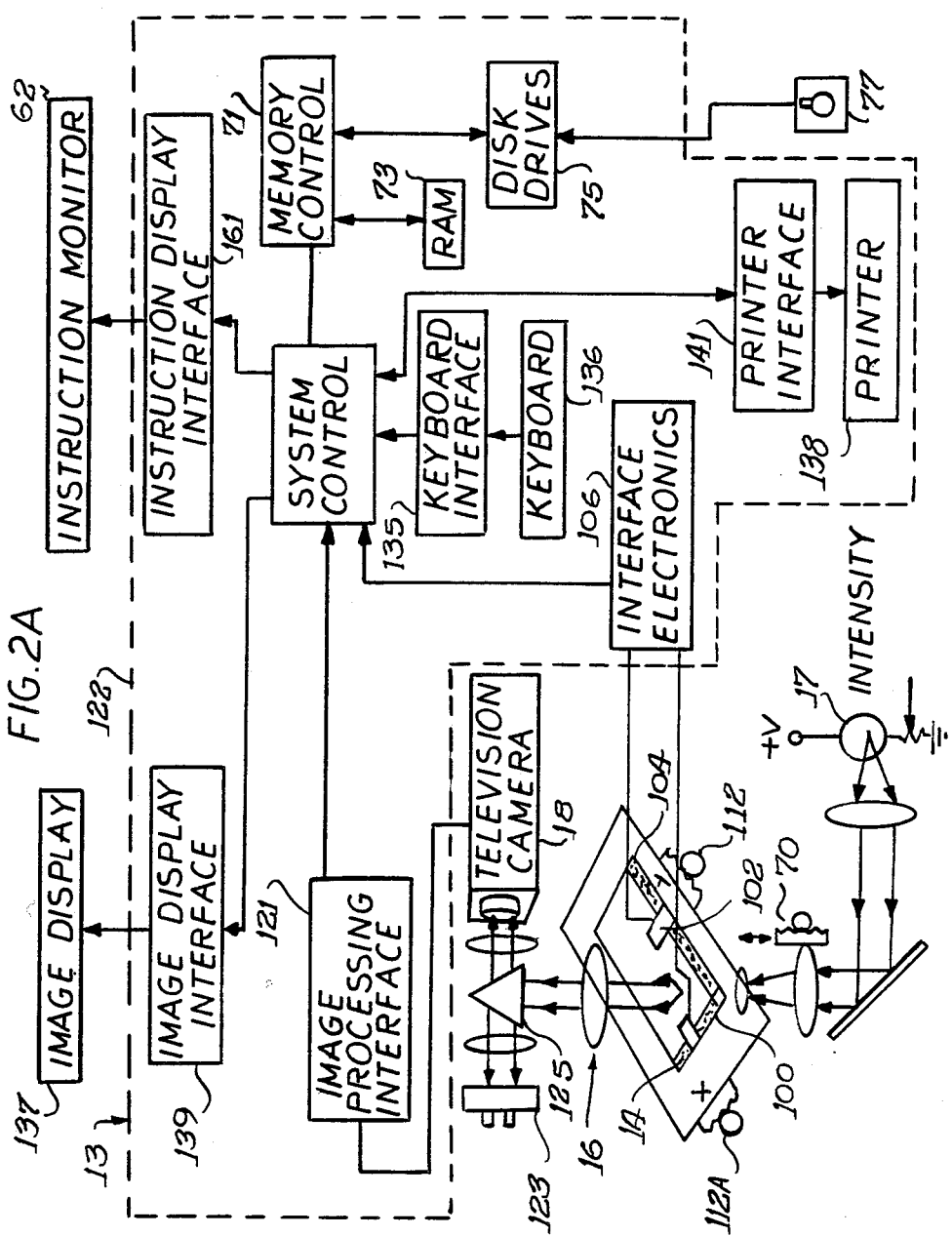
FIG. 2A is a functional block diagram of the image analysis system of FIG. 1.
Figure 4:
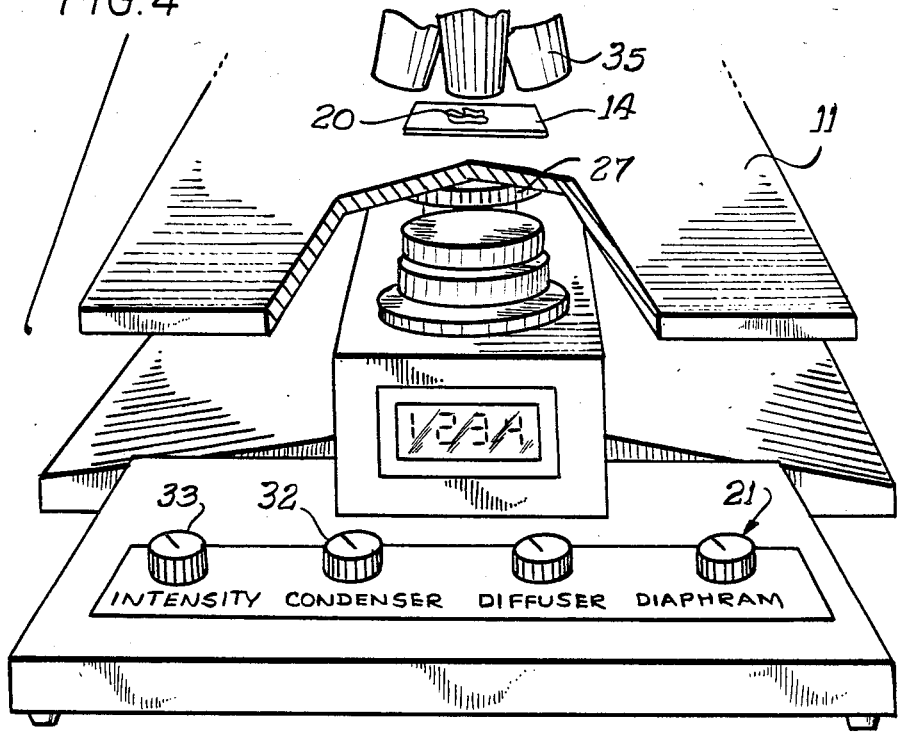
FIG. 4 is an enlarged fragmentary view of the microscope including operating controls for making adjustments.
Figure 5:
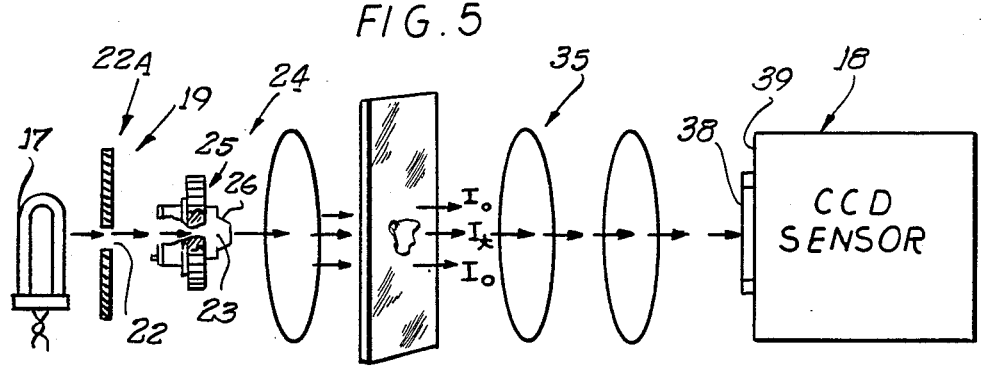
FIG. 5 is a diagrammatic illustration of the light controls for providing an image on the face of the CCD sensor.

As best seen in FIGS. 2A and 5, the light imaging system for the specimen 20 on the slide 14 includes an adjustable intensity or variable light source 17 which supplies light through field optics 19 which includes a variable field iris 22A which may be adjusted in size by operation of a control such as a control knob 21 shown in FIG. 4 which has a conventional wire leading back to the iris 22A and its control nut (not shown) which adjusts the size of the opening 22 (FIG. 5) for the field diaphragm or iris 18. Light having passed through the field optics 19 is then directed to the condenser optics 24 which includes an adjustable diaphragm or iris device 25 and condenser lenses 26 which are moveable vertically or in the Z direction by turning an outer adjustment ring 27 (FIG. 9).

The condenser iris or diaphragm device 25 is shown in considerable detail in FIGS. 8–11 and includes a central variable iris 28 through which the light passes between a series of leaves 29 which may be opened or closed to change the shape or the dimension of the variable iris opening 28 as will be described in greater detail hereinafter. At the front of the microscope is a suitable control 32 (FIG. 4) such as a knob labeled condenser the turning of which adjusts the position of the leaves 29 and the size of the variable aperture 28 through which the light passes into the lens 26 and then passes to the slide 14 on which is located the specimen 20. The image on the slide and the background light passes through an objective lens 35 and then passes to a beam splitter 31 (FIG. 2A) such as a prism which passes the light onto the television camera or CCD sensor 18 and up to the microscope eyepieces 23A. An image 38 of the cell specimen 20 is shown diagrammatically on the face 39 of the CCD sensor in FIG. 5; and it is this image which will be generating the analog signal which will be then converted to a digital signal which is representative of the mass of the substance being analyzed in the specimen such as DNA or hemoglobin or other material as will be hereinafter described.

The apparatus shown in FIG. 1 and described in the aforesaid patent application measures actual mass in actual true units such as picograms and reports out the same and it is important that the accuracy of the equipment be such that each of the various machines in the field if given the same slide would report out the same mass for the same cell being analyzed and that this mass be actual and a true mass of the constituent such as DNA or hemoglobin rather than a relative number. The problem with providing such consistent results and accuracy from machine to machine and from location to location using different operators at the various installations, such as in different pathology laboratories throughout the country, is that the light control used has a significant effect on the optical density of the image 38 on the face of the CCD sensor 18.

More specifically, the operator using the equipment may adjust the control 33 which is a knob labeled "intensity" in FIG. 4 to adjust the voltage for the lamp 17 which thereby controls the intensity of the light supplied to the optics. The operator at the station may also adjust the size of the field diaphragm by turning the knob 21 labeled diaphragm which is connected by a wire to the leads for the iris 22 of the field optics 19. The cone of light from the field iris is reduced in size to that which is the smallest needed to fully illuminate the specimen 20 so that there is a limited amount of background light being passed through the optics to the face of the CCD sensor 18. The cone of light, having been set at a particular size, is then passed through the condenser optics 24 at which is located the condenser iris which is controlled by the condenser variable knob 32 which is adjusted down to approximately one-third of the maximum opening, in this instance, by turning the control knob to move the iris leaves 29 inwardly, as shown in FIG. 11. This adjusts the condenser iris to a size which limits the amount of light which is passing through the transparent slide 20 at the area surrounding the specimen on the glass slide. The condenser lenses 26 are also movable in a vertical or "Z" direction by operating the control ring 27 shown in FIG. 9 for changing the optics until the proper focus of the field diaphragm iris is obtained and this therefore also controls the amount of light being passed onto and through the slide and eventually to the microscope eyepieces 23A and on to the face 39 of the CCD sensor 18. The above manipulations are performed while the operator views the cell image 40 on the monitor 37 for focus and light control. Thus it will be seen tat there are four different variables that need to be adjusted to control the intensity and amount of light which is hitting the microscope slide on which is mounted the specimen; and these four variables are the intensity of the light source, the size of the field iris or diaphragm, the size of the condenser iris or diaphragm, and the "Z" position of the condenser lenses.

Figure 3:
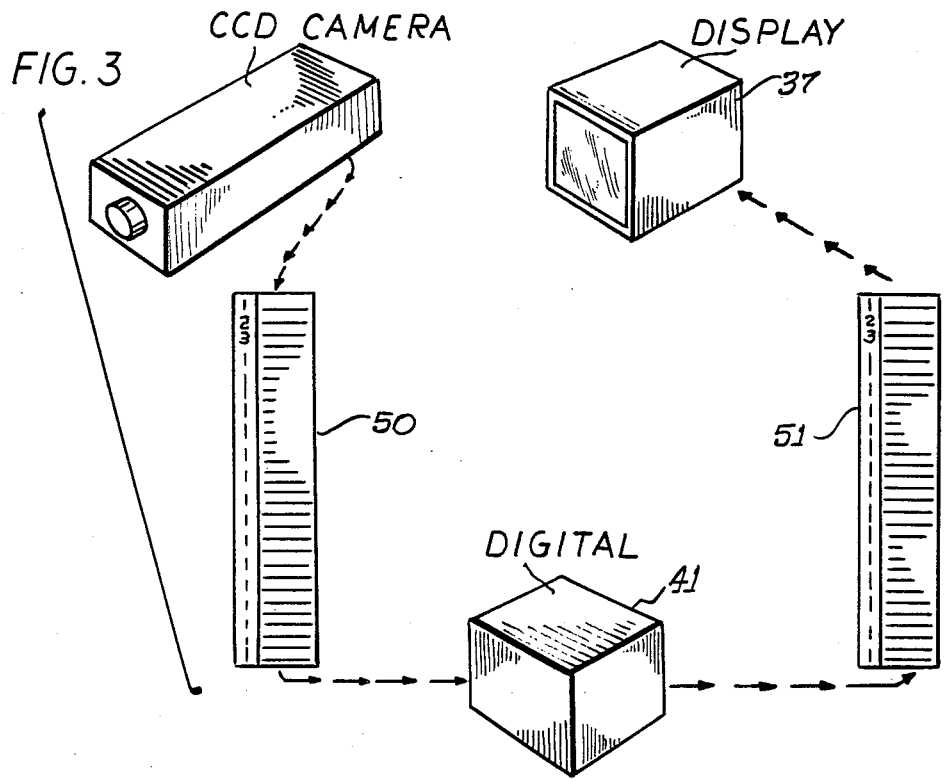
FIG. 3 is a diagrammatic illustration, of the CCD camera connected to the look-up tables and the digital computer and to an image display.

To obtain the accurate readings of actual mass units for the particular material being measured such as DNA, hemoglobin or the like, it is important that the amount of scattered light be limited in the analysis and that the scattered or background glare be fairly uniform from machine to machine and from operation to operation so that the results are all fairly accurate as to the particular mass actual being measured. Also, the amount of scattered light or glare should closely match the amount of glare or scattered light for which the optical density values in the look-up tables have been adjusted. As best seen in FIG. 5A, the light coming to the slide is designated $I_0$ as shown in the FIG. 5 and this is often termed hereinafter as the background light $I_o$ which passes readily through the transparent slide at the area about the specimen 20. At the specimen 20, some of the background light $I_0$ is absorbed and the light which is transmitted through the object is called transmitted light $I_t$. The $I_t$ passes through the objects to provide the image 38 on the face 39 of the CCD sensor. The transmitted light $T = I_t/I_o$. As the specimen thickness increases, the $I_t$ which is the light having passed through the cell decreases exponentially with increased thickness of the material being measured, for example DNA or hemoglobin. As will be explained in greater detail hereinafter in connection with FIGS. 2A and 3, the CCD camera provides a analog signal which is digitized by an analog to digital convertor and this digitized number from 1 to 256 is sent to a first look-up table 50 and the look-up table contains the optical densities each of which is a log transform equal to the formula $OD = -\log[T]$ where OD is the optical density and is the transmitted light where $T = I_t/I_o$. Thus, a log transform may be used directly by the digital computer for each of the pixels in the 512 × 512 pixel array without having to make exponential calculations with respect to finding the actual optical density for a given pixel. The CCD sensor 18 is preferably mounted on top of the microscope adjacent the eyepieces 23A and herein is a commercially available CCD camera although other cameras or sensors could be used. As best seen in FIG. 1, the cell image at the face of the CCD sensor 18 is seen by the operator of the apparatus as an image 40 (FIG. 1) on the display monitor 37. The image 40 is generated by the computer 41 and a second look-up table 51 which is connected to the display monitor 37. It will be appreciated that the background light $I_0$ which has passed through the transparent portion of the slide where there is no specimen and has passed through the optics may because of light scattering and imperfection in the lenses and in the tubes at an angle such that some scattered photons in the background light impinge at the area of the image 38 and thereby lessen the optical density at a pixel so that the pixel analog signal is in reality related to a less thick object or less mass than is actually present at the specimen 20. Because of the scattering and glare, it is most important that the light intensity be carefully controlled and that the glare be kept to a minimum and that the amount and intensity of glare or scattered light be kept relatively constant from machine to machine and from operation to operation on the same machine by the same or different operators.

Figure 6:
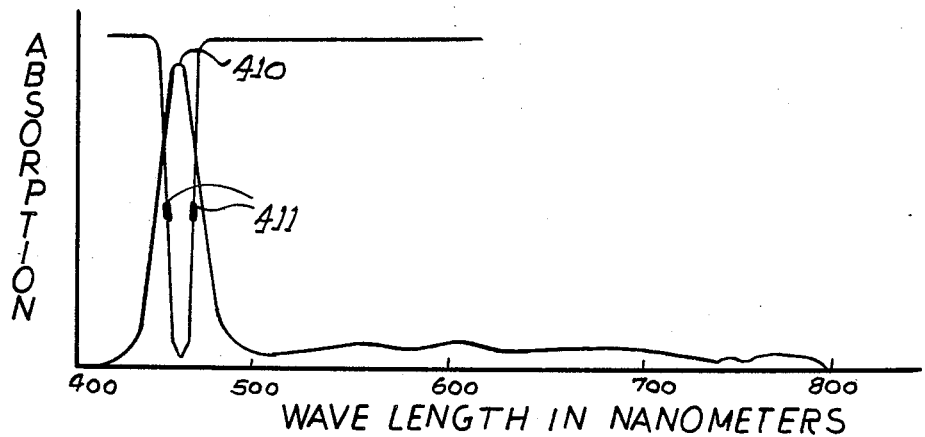
FIG. 6 is a graph showing absorption versus hemoglobin for a narrow pass band filter used with the apparatus shown in FIG. 5.
Figure 7:
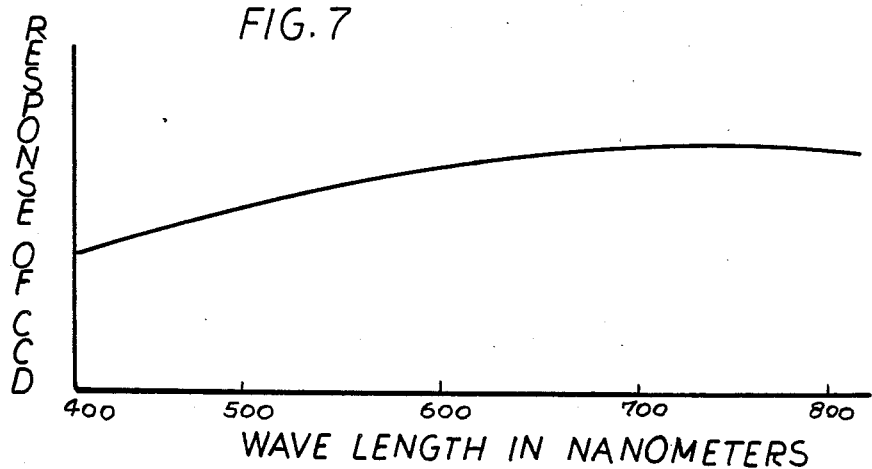
FIG. 7 shows that the CCD sensor will be affected by light from 400 through 800 nanometers.

An additional problem arises from the fact that not all of the wavelengths of light are at the peak wave e.g. 410 or 630 nanometers because the band pass filters used pass additional wavelengths of light. That is, the light $I_0$ and $I_T$ which provides the image 38 on face 39 of the CCD sensor 18 is filtered by a filter 43 which is a narrow bypass band filter of a particular wavelength, for example a 10 band wavelength pass filter for a 410 peak band wavelength Thus, the light impinging on the face 39 of the CCD sensor is not of all the same wavelength but may vary between 405 and 415 nanometers with the primary absorption for hemoglobin spectrum being at 410 nanometers. As diagrammatically illustrated in FIG. 7, the CCD sensor 18 when measuring hemoglobin has a relatively flat response line for generating light voltage, for light having wavelengths is within the range of 400 to 800 nanometers. Thus, whatever wavelengths of light are coming through in the 10 nanometer range filter will be effective. Herein, the ten nanometer filter width is measured as shown in FIG. 7 for a peak 410 nanometer wavelength at one-half of the peak 410 (FIG. 6) as indicated by the marks 411 in FIG. 6. Likewise for the feulgen blue azure stain and the DNA measurements, the filter is a 630 peak band pass filter with a 10 nanometer wide width.

In accordance with the present invention, there is provided a new and improved method and apparatus for reducing the amount of scattered light and providing a relatively constant amount and intensity of light at the face 39 of the CCD sensor 18 to produce more accurate and more consistent actual mass measurements from an optical density analysis of specimens 20 on a slide. This is achieved by optimizing light conditions by having the amount of and intensity of light relatively constant and reduced to that needed to do the specimen cell measurements and, in particular, without a large amount of extra light which results in more glare and more scattered light which adversely affects the optical densities and thereby the mass measurements which are preferably in real units such as picograms. Of the four different constants which can be changed, each of the constants is regulated in a manner to be hereinafter explained and particularly the condenser iris or aperture is controlled closely to provide a constant amount of light which is passing as background light through the slide 14. Furthermore, this constant amount of light is closely matched to the amount of light that was used when a glare correction was made for the values in the look-up tables, as will be explained.

The preferred manner of control of the condenser iris and the amount of light passing through the condenser iris is by a non-invasive technique to the light microscope such that the light microscope may be used in its normal manner; and, in so doing, one may adjust the size of the condenser iris between its normal fully opened to its fully closed position. The preferred non-invasive technique includes an attachment means or device which can be readily attached to the instrument to provide it with a fixed constant iris or aperture 23 to limit the amount of background light to that amount correlated to the particular condenser lenses being used. Without the attachment, the previously used adjustment procedure was to turn the knob 32 to the fully opened position so that the variable iris aperture 28 was at its largest diameter and then to turn the ring 27 in the opposite direction to reduce that aperture size by about one-third. A significant problem occurs that when the operator manually turns the knob to reduce the size of the aperture by one-third since that varies significantly in size which is not readily detected by the human eye and this causes a considerable difference in the background light and eventually scattered light which reaches the face 39 of the CCD sensor 18.

A very inexpensive and easily attachable and detachable means to provide a fixed iris 23 may be in the form of an attachable member or means 60 (FIG. 9) which includes a central cylindrical wall 61 which defines a fixed sized aperture 23. The fixed aperture 23 has a size which is reduced one-third from the maximum opening achieved for the variable condenser iris 28 when the leaves 29 are shifted to their fully opened position as shown in FIGS. 9 and 10. Thus, in operation the operator when adjusting the condenser iris will fully open the leaves 29 so that the leaves are no longer effective and the size of the iris opening 23 is then the size of the fixed iris opening in the member 60. Because the fixed iris and the variable iris are so closely adjacent as to almost be in the same horizontal plane, the difference in location of the fixed and variable iris does not make a substantial difference in this invention.

The method of adjusting the light for the four variables in accordance with the invention will now be described. The first adjustment that is made is that the operator will adjust the field iris 18 to make the cone of light as small as possible when viewing so that the amount of light which will ultimately end up on the face of the CCD sensor is kept to a reasonable value. The operator of the equipment will look through the microscope lens and adjust the knob 21 at the front of the microscope while viewing the cone of light to make it small as possible and still see the leaves of the diaphragm and then will stop adjusting with the knob 21. Then the operator will adjust the knob 32 to fully open the leaves 29 of the condenser variable iris 28 so that the fixed iris 23 becomes the controlling iris for the amount of light which is to pass through the condenser lenses 26. Next, the operator will turn the adjustment ring 27 to properly focus the condenser lenses while viewing the image 40 on the monitor 37. Also, the operator will adjust the light intensity by turning the knob 33 to provide a digital read-out at 65 (FIG. 4) at a predetermined voltage read-out, e.g. 8.3 volts. The operator then will view the image on an instruction display monitor 62 and displayed on the monitor will be a digital reading value for $I_o$. In this instance, it is desired that the $I_0$ be closely controlled the operator may again turn the light intensity knob 23 until $I_o$ reads 130 (or any predetermined value consistent with the input look up table) on the display monitor. The values in the look-up tables have been previously adjusted by using specimens which are dark objects of a known optical density and with the equipment adjusted to provide $I_o$ of 130, a reading is taken of the dark objects optical density from the CCD camera 18 and this optical density value is then compared to the known optical density value. Because scattered light photons at an $I_o = 130$ will be effecting image 38 at the face 39, the optical density value read will be less than the true optical density. After this analysis, the look-up tables are calibrated to give the true optical density value for when $I_o = 130$. Thus, the apparatus will be adjusted for light control and for reading out actual true mass with a minimum amount of error caused by scattered light or variations in light amount and intensity. Thus, this invention provides a true optical density read-out for each pixel in real time.

Referring now in greater detail to the illustrative and preferred embodiment of the invention, as shown in FIG. 2A, will now be described in greater detail.

Briefly, the apparatus 11 functions as a digital image processing system 113, FIG. 2A, and includes the conventional, commercially available, high resolution microscope, with which an operator can view specimens 20 on a support 14. As best seen in FIG. 2, the microscope stage 11 is movable incrementally by means 112 and 112A in X and Y directions for viewing various areas of the slide on the microscope platform or stage. The specimens or material on the slide are further viewable by the imaging system 13 which is controlled by a system control 122 in the form of a digital processor such as a personal computer 41. An operator can communicate with the system control 122 via keyboard 136

(FIGS. 1 and 2) and interacts with an apparatus 11 for viewing two displays. The first display, image display 37 is an RGB monitor which displays through the system control 22 the same image as seen through the microscope 15. A second display, instruction monitor 62, is another RGB monitor and is used to provide the operator with interactive prompts, messages, information, and instructions from the program controlling system control 122. A printer 138 is provided to produce a reliable hard copy output of the data produced by the apparatus 11.

The optics form an optical image of each of the cells on the slide and transmit them to an image splitter 125 which can take the form of a prism. On one side of the splitter 125, as seen in FIG. 2A, the television camera 18 or other detector converts the optical images point-by-point into a scanned electronic signal representing the optical intensity of each point in the image. The output of the camera 18, which is a standard NTSC analog video signal is applied to an analog to digital convertor 20 of an image processing interface 121. The image processing interface 121 converts the image signal from the television camera 18 to a digitized signal which is received and stored by the system control 122. Because of the continuous scanning, a real time image of the area of the optics are focused on is provided by the image display 37. In general, the image is a 512 × 512 array of pixels, each having a measured light intensity.

On the other side of the image splitter 125, are located the viewing optics 123 of the microscope 15. This parofocal arrangement allows the same image to be displayed on the image display 37. This feature allows the positioning of the platform 11 by manual X and Y adjustments means 12 and 12A until the operator views a field of interest on the slide 14. At that time, a computer enhanced digitized image of the selected field is displayed on the image display 37 for further analysis.

Both of the image displays 37 and 62 are controlled by a system control 122 through standard video interface circuitry 139 and 161, respectively. Similarly, the keyboard 136 and printer 138 communicate with the system control 122 through conventional interface circuitry 135 and 141, respectively. In addition, the system control 122 controls a random access memory 73 and bulk storage in the form of floppy and hard disk drives through memory control 71.

All of the interface circuits 121, 135, 139 and 141, 161, 71, and 106 can be selectively embodied on their own printed circuit boards which are mounted in the back plane or card connector of a conventional personal computer forming the system control 122. Preferably the personal computer can be one manufactured by the IBM corporation having a model designation AT. Such system control can be run under a disk operating system such as PC DOS version 3.1 or later. The system software for the image analysis is called an application program from the disk drive 75, and could, for example, be supplied on a floppy disk 77. The system software is read from the disk 77 and loaded into RAM 73. After loading program control is transferred to the analysis to regulate the various hardware elements previously set forth in a known manner and further description of this details of the invention may be found in the aforesaid co-pending patent application serial No. 927,285.

Referring to the fixed iris member 60 which is in the form of a cup-shaped member shown in FIGS. 8 and 9, it is generally a one piece body 79 of metal which has a bottom annular flange 80 with a hole 81 therein which receives a screw 82 which is threaded into a threaded opening or hole 83 in a depending circular member 84 on the microscope. The screw 82 may be readily unthreaded and then the cup shaped member 60 may be quickly slipped from engagement within a cylindrical wall 86 in the bottom of the cylindrical member 84. Herein, the cup shaped member 60 includes an upstanding cylindrical sidewall 87 mated in size to fit against the cylindrical wall 86. A small stepped shoulder 88 is formed on the cup-shaped member to fit against a stepped shoulder formed in the cylindrical 86. The fixed iris 23 in the upper wall 90 of the cup-shaped member 60 is sized to be the fixed diameter iris needed for the particular microscope condenser lenses. The size of the iris 23 has been calculated to be one-third less in area than the widest opening area for the variable iris 28 when the aperture is totally opened by opening the leaves 29 as far as possible, as shown in FIGS. 9 and 10. The cup has the effect that the fixed iris opening sets in approximately the same optical plane that the variable iris opening is in. It has been found that this one-third reduction provides about the best results for using the particular condenser lenses provided with the Reichert microscope.

The illustrated cup 60 is of one piece metal material and it is very inexpensive to manufacture and yet can be readily attached and detached with the one screw 82 so that it may not be viewed as an invasive member which will adversely affect the operation of the Reichert light microscope. The microscope, with the cup 60 removed, may function in its normal manner. Likewise, if there is any need for repair or assembly of the microscope, the microscope company will not have the excuse that it is not responsible for the cost of repair because of an invasive technique which has altered or modified the microscope.

Manifestly, the present invention is not limited to any particular microscope and various types of microscopes may be used from that disclosed. The Reichert microscope is used by way of example only and not by way of limitation. Rather than using the simple cup with the fixed aperture 23, other devices such as knobs, fixed stops for the variable leaves, or other devices could be used to allow for the variable apertures to be sized to a constant given value at the time of the cell analysis. However, such other equipment will either be invasive of the microscope or it will be substantially more costly than the attachment member 60 disclosed herein.

Thus, it will be seen from the foregoing that the present invention provides a new and improved method and apparatus for controlling the light where there are four variables which can be adjusted and which need to be adjusted, to optimize the actual true values or true densities being measured of a given material such as hemoglobin or DNA in actual cell specimens or in control cell objects as described in the aforementioned patent application. The controlling of the four light variables for the microscope has resulted in practically identical optical densities being obtained in real time for the same specimens being measured at different times by different operators on the same or different apparatus from the owner of this invention.

While a preferred embodiment has been shown and described, it will be understood that there is no intent to limit the invention by such disclosure, but, rather, it is intended to cover all modifications and alternative constructions within the spirit and scope of the invention as defined in the appended claims.

What is claimed is:

1. An apparatus using a light microscope for image analysis comprising:
   a CCD sensor having pixels receiving transmitted light having passed through the specimen and background light and for providing an optical density value based on received light at each pixel,
   a light source for illuminating a slide having a specimen thereon,
   means to adjust the light source to control the intensity of light being applied to the specimen on the slide and to the CCD sensor,
   a field iris for receiving light from the light source and a control means for adjusting the size of the field aperture in the field iris,
   a condenser optics means including a variable condenser iris which is adjusted to control the amount of light passing therethrough from the cone of light having passed through the field iris,
   a means for adjusting the variable condenser iris between a wide open and a substantially closed position,
   said condenser optics means being movable in a 37 Z" direction to adjust the focus of the light passing from the lenses and iris,
   means for supporting a slide having a specimen for receiving background light on one side of the slide and for providing transmitted light and background light on the opposite side of the slide for application to the face of the CCD sensor,
   means to fix the condenser iris at a predetermined size to assist in reducing the intensity and amount of light to a relatively constant amount with a limited amount of light scatted at the face of the CCD sensor,
   a computer connected to the CCD sensor to provide measured values of the background light, and
   a monitor connected to the computer for displaying the actual value of the background light so that the operator may adjust the means for adjusting the intensity of the light source to provide a numerical constant value for the background light.

2. An apparatus using a light microscope for image analysis comprising:
   a CCD sensor having pixels receiving transmitted light having passed through the specimen and background light and for providing an optical density value based on received light at each pixel,
   a light source for illuminating a slide having a specimen thereon,
   means to adjust the light source to control the intensity of light being applied to the specimen on the slide and to the CCD sensor,
   a field iris for receiving light from the light source and a control means for adjusting the size of the field aperture in the field iris,
   a condenser optics ;means including a variable condenser iris which is adjusted to control the amount of light passing therethrough from the cone of light having passed through the field iris,
   a means for adjusting the variable condenser iris between a wide open and a substantially closed position,
   said condenser optics ;means being movable in a "Z" direction to adjust the focus of the light passing from the lenses and iris,
   means for supporting a slide having a specimen for receiving background light on one side of the slide and for providing transmitted light and background light on the opposite side of the slide for application to the face of the CCD sensor,
   means to fix the condenser iris at a predetermined size to assist in reducing the intensity and amount of light to a relatively constant amount with a limited amount of light scatter at the face of the CCD sensor,
   the means to fix the iris at said predetermined size comprising a detachable member which has a fixed diameter opening, the size of the fixed condenser iris opening being a predetermined fraction of the size of the condenser variable iris when the condenser variable iris is fully opened.

3. An apparatus in accordance with claim 2 in which the fixed iris opening is about one-third less in size than the maximum wide open size for the variable iris.

4. An apparatus in accordance with claim 3 which said detachable member is a one-piece generally cup-shaped member having an opening in a top wall and having an attachment flange which may be secured to and detachably removed from the condenser optics.

5. An apparatus in accordance with claim 4 in which said cup-shaped member has a bottom wall with a threaded screw hole therein, and in which said cup shaped member has an opening whereby a threaded screw may be passed through the opening into the threaded hole so that the screw may readily attach and hold the cup-shaped member in position.

6. An image display apparatus for a slide for a specimen including in combination:
   a light microscope having a light bulb and control for light intensity,
   said light microscope having a variable condenser iris and a control for varying the size of the condenser iris,
   said light microscope having a field iris and a control for adjusting the size of the field iris to provide a cone of light passing from the light bulb into and through the condenser iris,
   condenser optic means including condenser lenses for condensing the light and for passing the light unto a transparent slide to provide the background light for the slide and for a specimen on the slide,
   a CCD camera having pixels each receiving the transmitted light having passed through the specimen and for receiving the background light,
   means for transforming the analog signals provided from the camera into log transforms providing an optical density value for each of the pixels,
   a digital processing means for performing a true accurate measurement in actual mass units from the log transforms values,
   means operable by the digital computer for converting the log transforms numbers back into real time digital signals,
   display monitor means connected to said means for conversion to receive the digital signals and to provide a real time image of the specimen for review, and
   means in said digital computer for providing a background light intensity value on said display monitor means so that the operator may adjust the intensity of the light to a predetermined value for the background light at the slide.

7. An apparatus in accordance with claim 6 in which a cup having a fixed aperture is attached to the variable condenser lenses, said variable condenser iris being capable of being opened by the operator to a size larger than the fixed aperture size so that the latter controls the amount of light being applied as background light to the slide.

8. An apparatus in accordance with claim 7 in which a fastening means fastens the fixed iris member for easy attachment and removal from the condenser means.

* * * * *